United States Patent

Klein et al.

[11] Patent Number: 5,924,995
[45] Date of Patent: Jul. 20, 1999

[54] NON-INVASIVE METHOD FOR THE FUNCTIONAL ASSESSMENT OF INFANTS AND CHILDREN WITH AN INHERITED METABOLIC DISORDER

[75] Inventors: Peter D. Klein, Houston, Tex.; Louis J. Elsas, II, Atlanta, Ga.

[73] Assignee: Meretek Diagnostics, Houston, Tex.

[21] Appl. No.: 08/967,555

[22] Filed: Nov. 10, 1997

[51] Int. Cl.⁶ .................................................. A61B 5/08
[52] U.S. Cl. .......................................... 600/532; 600/531
[58] Field of Search .................................. 600/529, 531, 600/532; 422/84; 73/23.3

[56] References Cited

U.S. PATENT DOCUMENTS

| | | | |
|---|---|---|---|
| 4,619,269 | 10/1986 | Cutler et al. ............................. | 128/719 |
| 5,140,993 | 8/1992 | Opekun, Jr. et al. ................... | 128/730 |
| 5,178,155 | 1/1993 | Mault ....................................... | 128/718 |
| 5,445,160 | 8/1995 | Culver et al. ............................ | 128/719 |

OTHER PUBLICATIONS

Elsas LJ, Ellerine NP, Klein PD. Practical Methods To Estimate Whole Body Leucine Oxidation in Maple Syrup Urine Disease. Pediatric Research published 1993; vol. 33, No. 5, pp. 445–451.

Ellerine NP, Herring W, Elsas LP II, McKean MC, Klein PD, Danner DJ, Thiamin–Responsive Maple Syrup Urine Disease In A Patient Antigenically Missing Dihydrolipoamide Acyltransferase. Biochemical Medicine and Metabolic Biology, published 1993; vol. 49, pp. 363–374.

Berry GT, Nissim I., Gibson JB, Mazur AT, Lin Z, Elsas LJ, Singh RH, Klein PD, Segal S. Quantitative Assessment of Whole Body Galactose Metabolism In Galactosemic Patients. Eur J. Pediatr (1997) Suppl 1); pp. S43–S49.

*Primary Examiner*—John G. Weiss
*Assistant Examiner*—Charles W. Anderson
*Attorney, Agent, or Firm*—Browning Bushman

[57] ABSTRACT

A non-invasive method for the functional assessment of an inherited metabolic disorder in infants and children including administering to the patient a predetermined substrate labeled with a stable non-radioactive isotope of carbon $^{13}C$, analyzing the breath samples for the isotopic abundance of $^{13}CO_2$, and calculating the quantity of substrate oxidized for determining the rate of substrate oxidation.

20 Claims, 2 Drawing Sheets

NON-INVASIVE METHOD FOR THE FUNCTIONAL ASSESSMENT OF INFANTS AND CHILDREN WITH AN INHERITED METABOLIC DISORDER

FIELD OF THE INVENTION

This invention relates to a non-invasive method for the functional assessment of infants and children with an inherited metabolic disorder, and more particularly to such a method in which the oxidation of a substrate is used to estimate whole body capacity reflecting the disorder.

BACKGROUND OF THE INVENTION

Newborn infants are routinely screened for the presence of inherited metabolic disorders. These disorders are the consequence of a gene mutation which alters or inactivates a key enzyme in the metabolism of a nutrient such as a carbohydrate or amino acid. One of the most common of such disorders is galactosemia which occurs in 1 of every 8700 live births. Classical galactosemia is a potentially lethal disease caused by mutations which impair galactose-1-phosphate uridyl-transferase (GALT) (enzyme classification 2.7.7.12). This enzyme catalyzes the second step in the critical metabolic sequences which convert galactose to glucose. Since the newborn infant's principle nutritional energy source is lactose (disaccharide of glucose and galactose), this pathway is critical both for energy from glucose-1-phosphate oxidation and for uridyl diphosphate-galactose as a source for posttranslational galactosylation of membrane proteins in the rapidly growing infant.

Deficiency can lead to catastrophic events in the newborn with symptoms progressing from poor feeding, prolonged jaundice, bleeding diathesis and cataracts to *E. coli* sepsis and death. The simple exclusion of galactose from the newborn diet halts this toxic progression and is lifesaving. One may anticipate that the sooner in the newborn's life the diagnosis is suspected and the dietary change to sucrose-based (soy) formula is made, the better the short-term outcome in preventing neonatal death.

Long term outcome in children with galactosemia is more complex. Many older children have growth and developmental delays, verbal dyspraxia, and ovarian failure regardless of the age at which dietary intervention was accomplished. One of the factors determining outcome is the degree of GALT impairment. Following cloning and sequencing of the GALT gene, over 90 variations have been detected which produce different degrees of impairment. Some of these mutations produce partial but not total ablation of GALT enzyme activity.

At present, newborn screening is carried out for GALT using enzyme linked methods on blood samples obtained by heel stick and blotted on filter paper. This process measures enzyme activity in the red blood cell which is non-nucleated and possesses no protein synthesis capability. If the GALT enzyme is destabilized by a mutation or is inactivated by high environmental temperatures during transport of the sample, it will result in return of a positive galactosemic result even if clinically significant amounts of GALT are present. Follow-up screening by biochemical phenotyping and molecular genotyping are then required to characterize the positive screening result. In a recent study of 1.7 million newborns in Georgia, 2,463 were "positive", and 384 were determined to have impaired GALT producing a false positive rate of 84%. Of the 384 with abnormal GALT, 180 had clinically significant galactosemia, defined as GALT activity below 10% of control with classical galactosemia and these were placed on galactose-free diets.

From the foregoing it is evident that the present methodology of newborn screening has high sensitivity but low specificity in establishing the degree of GALT impairment in the infant. What is required is the ability to measure enzyme function as it exists within the individual.

SUMMARY OF THE INVENTION

The present invention to directed to a method for providing a non-invasive functional assessment of whole-body galactose oxidation capacity. This assessment provides a quantitative estimate of the rate of galactose oxidation that reflects the degree of somatic impairment in the GALT enzyme. When used in the first two weeks of life, this test identifies individuals at highest risk from continued galactose consumption. When used in children with partial GALT impairment, the rate of whole-body galactose oxidation provides the physician with a scalar of impairment to be used in patient management.

DESCRIPTION OF THE INVENTION

Figure 1:
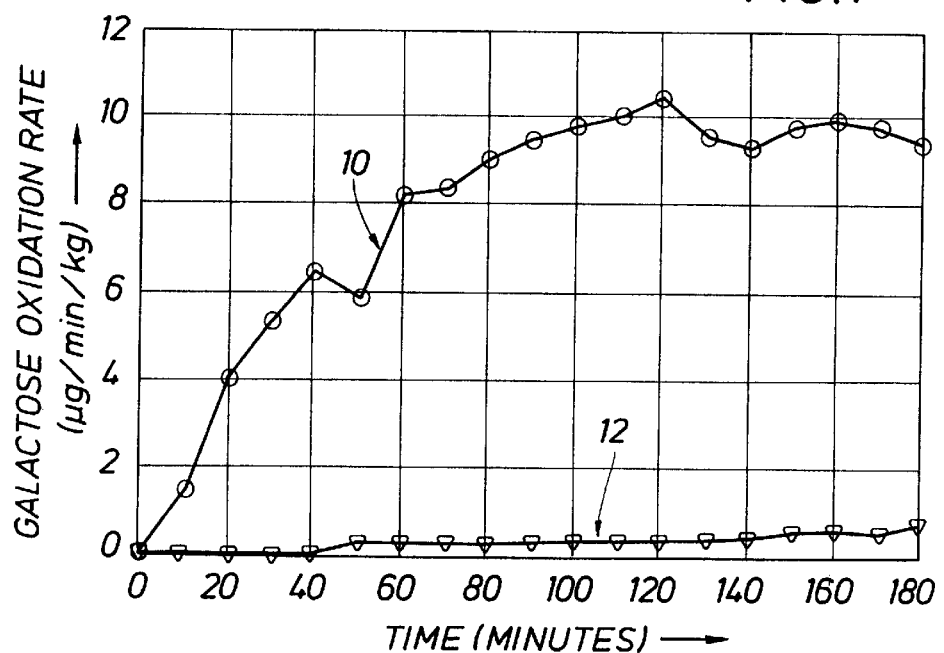
FIG. 1 is a graph illustrating the galactose oxidation rate in two patients, one being normal and the other shown by DNA-typing to be a homozygous deficient genotype.

The invention is directed particularly to a non-invasive method for the functional assessment of an inherited metabolic disorder in which the whole-body galactose oxidation capacity is measured by the method to identify infants at highest risk from continued galactose consumption. The method may be carried out in five steps as set forth below.

Step one: Collection of baseline breath sample.

A sample of end-tidal air is collected from the child or infant. For newborn infants, the preferred collection method includes the breath collection device described in U.S. Pat. No. 5,140,993 dated Aug. 25, 1992, entitled "Device for Collecting a Breath Sample" and equipped with a neonatal resuscitation mask with a one-way inlet valve. The infant's exhaled breath is collected in the collection bag and transferred to an evacuated storage tube, preferably 5 ml in volume. Older children are capable of blowing directly into the collection bag; or alternatively, they can blow through a straw extending to the bottom of the storage tube when the stopper has been removed. The stopper is replaced after breath collection.

Step 2: Administration of test substrate:

The test substrate includes galactose which has been labeled with a stable non-radioactive isotope of carbon, $^{13}C$ in the C-1 or C-2 position, and is administered to the patient or test subject in a dosage of approximately 5 mg per kg subject body weight by an oral or intravenous route, the oral route being preferred. While a $^{14}C$ isotope of carbon could be utilized in the present invention, a harmful effect to infants could result from the radioactive material.

Step 3: Collection of post-dose breath samples

Using the same techniques employed in Step one, serial breath samples are preferably collected over the next two hours at intervals of 10–15 minutes. For accurate test results, a minimum of five samples are desirable. While a time period of 120 minutes is preferred, shorter or longer time periods between about 60 minutes and 240 minutes may be utilized in a satisfactory manner. Also, while a time interval of 10–15 minutes is preferred, shorter or longer time intervals may be utilized but the time interval should not exceed about 30 minutes and should be precisely calculated. The minimum number of samples required to be collected after substrate administration is one but this does not preclude the use of continuous monitoring of the subject's breath in a flow system equipped with isotopic detection capability.

Step 4: Analysis of $^{13}C$ isotopic abundance of $^{13}CO_2$ of breath samples The breath samples are analyzed for the isotopic abundance of $^{13}CO_2$ ($^{13}CO_2/^{12}CO_2$), preferably by gas isotope ratio mass spectrometry but equally well by any method which can determine the concentration of $^{13}CO_2$ to within 1%.

Step 5: Calculation of rate of substrate oxidation

Three quantities are used in these calculations: 1) the post-dose enrichment over the baseline value of the breath for each of the breath samples collected over a preferable time period of 120 minutes, 2) the rate of $CO_2$ production adjusted for the age, sex, height and weight of the subject, and 3) the weight of substrate administered. These values are used in conventional equations to determine the rate of substrate oxidation as percent dose per minute or as $\mu g$ substrate/min/kg body weight. Suitable equations may include the calculation of $CO_2$ production from the basic metabolic rate as follows:

| Basal Metabolic Rate (Megajoules/d) by age, sex, weight (kg) and height (m) | | |
|---|---|---|
| Age (y) | Sex | Equation |
| 0–10 | M | BMR = 0.082 W + 0.545 H + 1.736 |
|  | F | BMR = 0.071 W + 0.677 H + 1.533 |
| 10–18 | M | BMR = 0.068 W + 0.574 H + 2.157 |
|  | F | BMR = 0.0035 W + 1.948 H + 0.837 |
| 18–30 | M | BMR = 0.063 W − 0.042 H + 2.943 |
|  | F | BMR = 0.057 W + 1.184 H + 0.411 |
| 30–60 | M | BMR = 0.048 W − 0.011 H + 3.670 |
|  | F | BMR = 0.0344 W + 0.006 H + 3.530 |

Energy Expenditure
EE=1.4 BMR×2.39 (Cal/MJ)
EE(kcal/d)=22.4 (L/mol)[1.106×$VCO_2$(mol/d)+3.91×$VO_2$(mol/d)
Respiratory Quotient in fasting state($VCO_2/VO_2$)=0.80
$CO_2$ production
$VCO_2$ (mol/d)=EE/134.25
$CO_2$ production ($\mu M/kg/min$)=($VCO_2 \times 10^6$)/24 h×60 min×wt The calculation of dose oxidized from delta over baseline (DOB) and $CO_2$ production may be as follows:

$$\text{Percent dose oxidized/min} = \frac{(DOB/1000 \times 0.0112372 \times CO_2 \text{prod})}{(\text{dose}/MW)}$$

where 0.0112372 in the isotopic abundance of the $^{13}C$ reference standard, Pee Dee Belemnite, dose is 5 mg×kg body weigh, the molecular weight of $^{13}C$ galatose is 181

Galactose oxidation, $\mu g/min/kg$=Percent dose oxidized per min×5000

The values obtained in accordance with the above equations are compared to standard values obtained from normal children to obtain a numerical estimation of whole body enzyme function.

FIG. 1 illustrates the whole-body oxidation of 1-$^{13}C$ galactose by two 14-year-old females of which one (N/N) is normal as illustrated by line 10 and the other (Q188R/Q188R) as illustrated by line 12 has been shown by DNA-typing to be a homozygous deficient genotype. The time course of the substrate oxidation is evident from lines 10 and 12 for the normal subject as well as the demonstration of the absence of whole-body activity in the homozygous deficient subject.

Table 1 shows that a wide range of whole-body galactose oxidation capacity exists in subjects in whom various galactosemic mutations have been identified initially by red blood cell screening and subsequent DNA-typing. Many variations have near normal levels of whole-body galactose oxidation.

TABLE 1

Whole-Body 1-$^{13}C$ Galactose Oxidation in PO Breath Test by Genotype

| Patient | Genotype | $\mu g/min/kg$ |
|---|---|---|
| CH | Q188R/Q188R | 0.20 |
| JL | Q188R/Q188R | 0.31 |
| CD | Q188R/V157A | 1.53 |
| MD | Q188R/S135L | 8.13 |
| JoL | Q188R/N | 9.02 |
| VH | S135L/N | 7.65 |
| SH | S135L/N | 9.10 |
| ShH | S135L/S135L | 8.97 |
| RJ | S135L/Unknown | 9.44 |
| KS | N314D/N | 9.59 |
| JV | N134D/Q188R | 11.34 |
| JH | N/N | 7.81 |
| BJ | N/N | 8.85 |
| JM | N/N | 10.40 |
| JW | N/N | 12.05 |
| MR | N/N | 12.74 |
| NM | N/N | 13.40 |

Table 2 shows that characterization of whole body galactose oxidation in the genotypes can be accomplished with galactose labeled either in the C-1 or C-2 position.

TABLE 2

Whole-Body Oxidation of 1-$^{13}C$- and 2-$^{13}C$-Galactose by Various Genotypes

| Genotype | Mode | 120 min $\mu g/min/kg$ | 120 min $\mu g/min/kg$ |
|---|---|---|---|
| Q188R/Qi88R | iv | 0.79 | 0.62 |
| Si35L/Normal | iv | 5.36 | 6.87 |
| Si35L/S135L | iv | 5.39 | 7.53 |
| N314D/N314D | iv | 8.85 | 7.61 |
| N/N | iv | 5.39 | 7.92 |
| N/N | iv | 8.45 | 8.44 |

Table 3 shows that the route of administration of the substrate does not affect the genotype classification and that the oral (PO) route provides an excellent response in all genotypes tested.

TABLE 3

Comparison of Whole-Body Galactose Oxidation After IV and PO 1-$^{13}C$-Galactose Administration by Genotype

| Patient | Genotype | IV 120 min $\mu g/min/kg$ | PO 120 min $\mu g/min/kg$ | PO/IV Ratio |
|---|---|---|---|---|
| CH | Q188R/Q188R | 0.79 | 0.20 | 0.25 |
| JL | Q188R/Q188R | 0.26 | 0.31 | 1.18 |
| VH | Si35L/Normal | 5.36 | 7.65 | 1.43 |
| SH | Si35L/S135L | 5.39 | 8.97 | 1.66 |

TABLE 3-continued

Comparison of Whole-Body Galactose Oxidation After
IV and PO 1-$^{13}$C-Galactose Administration by Genotype

| Patient | Genotype | IV 120 min μg/min/kg | PO 120 min μg/min/kg | PO/IV Ratio |
|---|---|---|---|---|
| JL | Q188R/N | 6.77 | 9.02 | 1.33 |
| SK | N314D/N | 9.38 | 9.59 | 1.02 |
| JH | N/N | 8.45 | 7.81 | 0.92 |
| JM | N/N | 5.39 | 10.40 | 1.93 |
| MR | N/N | 4.95 | 12.74 | 2.58 |
| Average | | | | 1.37 |

Table 4 shows the application of this method using an oral dose of 1-$^{13}$C-galactose to infants within the first two weeks of life. This is the interval within which initial positive newborn screening results must be verified to determine the degree of impairment associated with the mutation. The results show that the levels of whole-body galactose oxidation present can be demonstrated even at this age.

TABLE 4

Whole-Body 1-$^{13}$C-Galactose Oxidation by Newborn Infants

| Infant | Category | Age-d | 120 min μg/min/kg |
|---|---|---|---|
| RW | White female | 1 | 17.07 |
| JS | Hispanic female | 1 | 13.86 |
| YM | Hispanic female | 2 | 10.64 |
| QB | Black male | 2 | 15.75 |
| EJM | Black male | 2 | 13.04 |
| BDLT | Hispanic male | 7 | 12.37 |
| LB | Black female | 11 | 12.55 |
| RPJ | White female | 11 | 12.77 |

Figure 2:
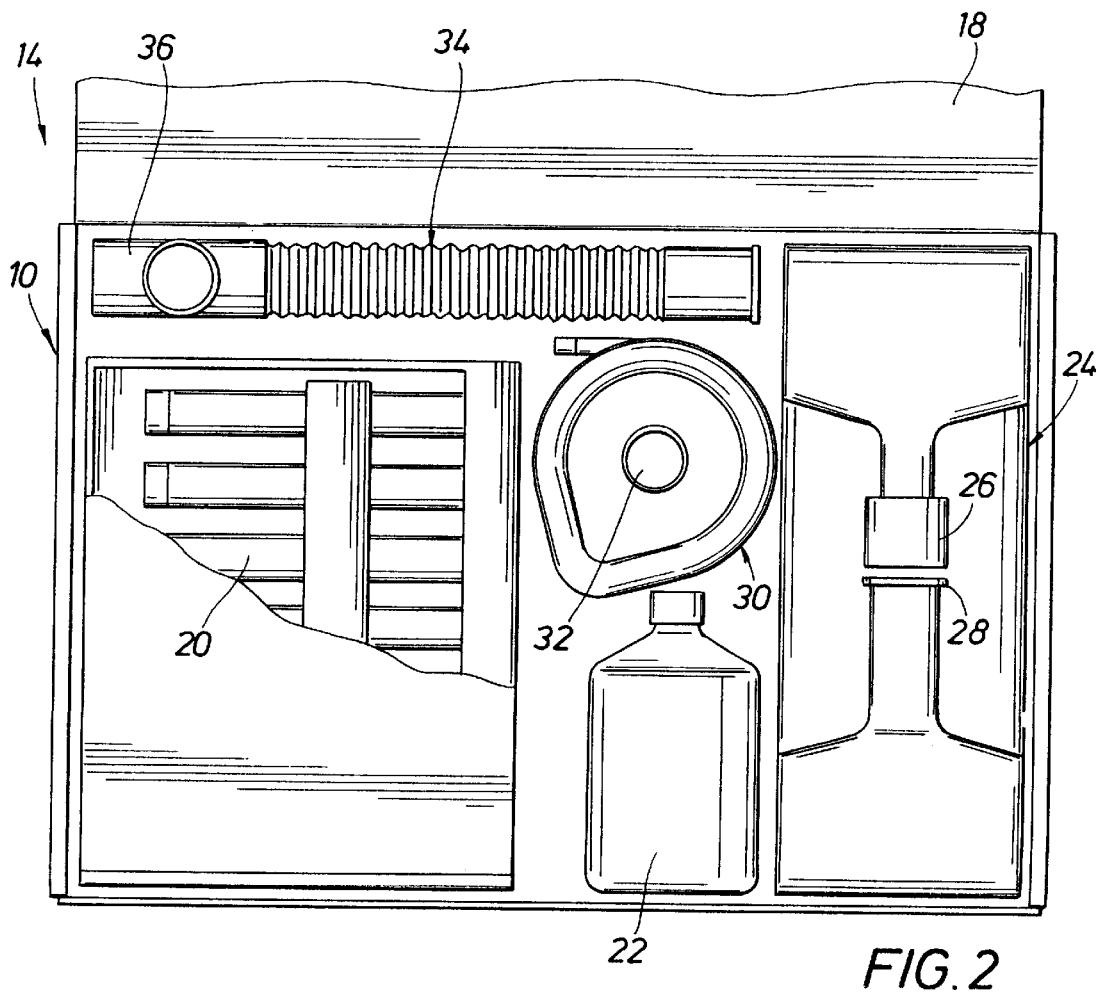
FIG. 2 is a schematic view of a kit for measuring whole-body galactose oxidation in infants.
Figure 3:
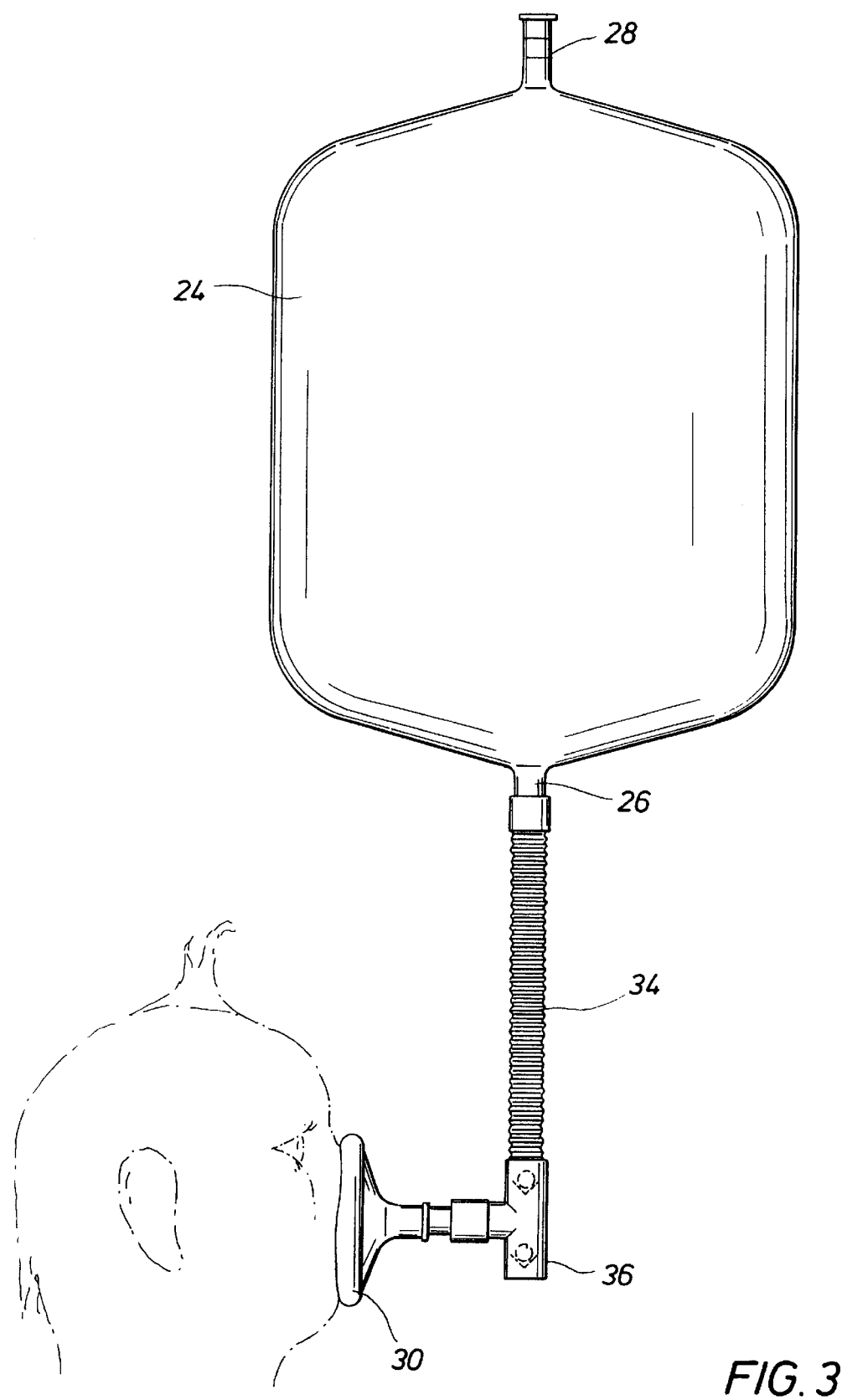
FIG. 3 is a schematic view of the breath sample collective device in operable position for an infant.

FIG. 2 illustrates schematically a kit for measuring whole-body galactose oxidation in infants. The kit indicated generally at 14 comprises a paperboard rectangular box 16 having a folding cover 18. Positioned within box 16 are a small box 20 of sample tubes 21 and a small bottle 22 of a substrate such as galactose. A folded breath collector bag 24 having an inlet 26 and an outlet 28 is provided similar to the breath sample collecting device illustrated in U.S. Pat. No. 5,140,993 dated Aug. 25, 1992, the entire disclosure of which is included for all purposes. A neonatal resuscitation mask for an infant is shown at 30 having a nipple 32. A connector is shown at 34 having a one way check valve 36 to permit air to be inhaled from atmosphere but preventing air from being exhaled to atmosphere. The breath sample collecting device is shown in operable relation in FIG. 3 with mask 30 over the mouth of an infant. Air is inhaled from atmosphere at the end of check valve 36 and exhaled through connector 34 to bag 24. The exhaled breath in bag 24 upon completion of the sample from the infant is positioned within a sample tube 21 for analysis of the $CO_2$ content such as by a gas isotope ratio mass spectrometry.

The substrate may, alternatively, be labeled with radioactive isotopes of carbon, specifically $^{14}$C, and the concentration of the labeled carbon dioxide could be determined from the detected radioactivity in breath. However, radioactive isotopes are not suitable for use in infants or children but could be used in adult subjects.

It can be readily appreciated that the detection of $^{13}CO_2$ required in this method is not limited to the use of gas isotope ratio mass spectrometry but that any analytical determination of the ratio of $^{13}CO_2$ to $^{12}CO_2$ with the ability to detect changes of 1% or less in the $^{13}CO_2$ abundance in breath may be employed. This includes but is not limited to the use of the infrared spectral properties of $^{13}CO_2$ and $^{12}CO_2$.

From the above, it is apparent that a suitable non-invasive method for functional assessment of infants and children with an inherited metabolic disorder has been provided. The method is easily carried out by (1) the collection of a breath sample from the patient, (2) administering to the patient a galactose substrate labeled with a non-radioactive isotope of carbon such as $^{13}$C, (3) collecting from the patient at precise intervals over a predetermined precise time period a plurality of additional breath samples; (4) analyzing the breath samples for their isotopic abundance of $^{13}CO_2$ ($^{13}CO_2/^{12}CO_2$); and (5) calculating the post-dose enrichment over the baseline value of the breath of each sample and adjusting for the age, sex, height, weight and dose of galactose substrate used.

The whole-body oxidation of the galactose substrate labeled with a carbon isotope indicates to a physician the degree of impairment associated with a particular genotype of inherited metabolic disorder and identifies those most critically dependent on dietary intervention. Kit 14 has been provided particularly for infants for measuring the whole-body galactose oxidation to determine the extent of an inherited metabolic disorder.

While the method of this invention has been illustrated as directed particularly to infants and children with galactosemia, this method is applicable to any other inherited metabolic disorder in which the oxidation of a substrate or the output of labeled $CO_2$ can be used to estimate whole-body capacities reflecting the disorder. These include but are not limited to phenylketonuria (oxidation of labeled phenylalanine substrate), maple syrup urine disease (oxidation of labeled leucine substrate) or disorders of thyroid function (recovery of labeled bicarbonate substrate as $CO_2$). It is apparent that some of the steps in this invention may be changed or modified without departing from the inventive concepts involved. However, it is the aim of the appended claims to cover all such changes and modifications fully within the true spirit and scope of the present invention.

What is claimed is:

1. A non-invasive method for the functional assessment of an inherited metabolic disorder in infants and children; said method comprising the following steps:
    collecting a breath sample from a patient;
    administering to the patient a predetermined dosage of a predetermined substrate labeled with a stable non-radioactive isotope of carbon;
    repeating the collection of breath samples from the patient after administering the substrate at predetermined time intervals over a predetermined time period for the collection of a plurality of breath samples after administering the substrate;
    analyzing the breath samples for the isotopic abundance of $^{13}CO_2$; and
    calculating the quantity of substrate oxidized for determining the rate of substrate oxidation.

2. A non-invasive method as set forth in claim 1 wherein the step of administering a dosage of a substrate includes a substrate labeled with an isotope of carbon $^{13}$C.

3. The non-invasive method as set forth in claim 1 wherein the step of calculating the quantity of substrate oxidized includes adjusting the rate for the age, sex, weight of patient and weight of substrate administered.

4. The non-invasive method as set forth in claim 1 wherein the step of repeating the collection of breath samples includes repeating the collection of at least five breath samples at time intervals less than about 30 minutes.

5. The non-invasive method as set forth in claim 1 wherein the step of repeating the collection of breath samples includes repeating the collection of breath samples at time intervals between about 10 to 15 minutes.

6. A non-invasive method as set forth in claim 1 wherein the step of administering a predetermined substrate includes administering a galactose substrate.

7. The non-invasive method as set forth in claim 1 wherein the step of administering a predetermined substrate includes administering a galactose substrate orally.

8. The non-invasive method as set forth in claim 1 wherein the step of administering a predetermined substrate includes administering a galactose substrate intravenously.

9. The non-invasive method as set forth in claim 1 wherein the step of administering a predetermined substrate includes administering a phenylalanine substrate.

10. The non-invasive method as set forth in claim 1 wherein the step of administering a predetermined substrate includes administering a leucine substrate.

11. The non-invasive method as set forth in claim 1 wherein the step of administering a predetermined substrate includes administering a bicarbonate substrate.

12. The non-invasive method as set forth in claim 1 wherein the step of analyzing the breath samples includes measuring the proportion of $^{13}CO_2$ to $^{12}CO_2$ in $CO_2$ samples.

13. The non-invasive method as set forth in claim 1 wherein the step of analyzing the breath samples includes analyzing the breath samples by gas isotope ratio mass spectrometry.

14. A non-invasive method for the functional assessment of an inherited metabolic disorder in infants and children; said method comprising the following steps:

collecting a breath sample from a patient;

administering to the patient a predetermined dosage of a galactose substrate labeled with a stable non-radioactive isotope of carbon $^{13}C$;

repeating the collection of breath samples from the patient after administering the substrate at predetermined time intervals over a predetermined time period for the collection of at least five breath samples after administering the substrate;

analyzing the breath samples for the isotopic abundance of $^{13}CO_2$; and calculating the quantity of galactose substrate oxidized for determining the rate of galactose oxidation.

15. The non-invasive method as set forth in claim 14 wherein the step of calculating the quantity of the galastose substrate oxidized includes adjusting the rate for the age, sex, weight of patient and weight of the galastose substrate administered.

16. The non-invasive method as set forth in claim 14 wherein said step of analyzing the breath samples includes measuring the proportion of $^{13}CO_2$ to $^{12}CO_2$ samples.

17. A non-invasive method for the functional assessment of an inherited metabolic disorder in an infant or child utilizing a hand carried kit, said kit having a plurality of sample breath tubes, a container of substrate, a breath collector bag, a face mask for the infant or child for inhaling and exhaling, and a connector between the face mask and breath collector bag including a check valve to permit inhaling of air from atmosphere and to permit exhaling into the breath collector bag; said method including the following steps:

assembling said breath collector bag, face mask and connector;

then placing said face mask over the mouth of the infant or child;

collecting a breath sample in said breath collector bag from the child or infant;

then administering to the child or infant a predetermined dosage of a predetermined substrate labeled with a stable non-radioactive isotope of carbon;

repeating the collection of breath samples in said bag from the infant or child after administering the substrate at predetermined time intervals over a predetermined time period for the collection of a plurality of breath samples after administering the substrate;

analyzing the breath samples for the isotopic abundance of $^{13}CO_2$; and calculating the quantity of substrate oxidized for determining the rate of substrate oxidation.

18. The non-invasive method as set forth in claim 17 wherein the step of calculating the quantity of substrate oxidized includes adjusting the rate for the age, sex, weight of patient and weight of substrate administered.

19. The non-invasive method as set forth in claim 18 wherein the step of repeating the collection of breath samples includes repeating the collection of at least five breath samples at time intervals less than about thirty minutes.

20. The non-invasive method as set forth in claim 17 wherein the step of analyzing the breath samples includes measuring the proportion of $^{13}CO_2$ to $^{12}CO_2$ in $CO_2$ samples.

* * * * *